United States Patent
Fang et al.

(10) Patent No.: US 8,937,284 B2
(45) Date of Patent: Jan. 20, 2015

(54) CONTROL AND SENSING SYSTEM FOR DIFFUSION OPTICAL TOMOGRAPHY AND METHOD FOR OPERATING THE SAME

(75) Inventors: Wai-Chi Fang, Hsinchu (TW); Tien-Ho Chen, Hsinchu (TW); Shih Kang, Hsinchu (TW); Shih-Yang Wu, Hsinchu (TW); Ching-Ju Cheng, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 273 days.

(21) Appl. No.: 13/524,420

(22) Filed: Jun. 15, 2012

(65) Prior Publication Data
US 2013/0155389 A1    Jun. 20, 2013

(30) Foreign Application Priority Data
Dec. 14, 2011 (TW) .............................. 100146129 A

(51) Int. Cl.
*G01J 5/10*    (2006.01)

(52) U.S. Cl.
USPC ...................................... 250/338.1

(58) Field of Classification Search
USPC ........... 250/338.1, 458.1, 459.1; 356/432, 51; 600/425
See application file for complete search history.

(56) References Cited

PUBLICATIONS

Kang et al., "Advanced Green Energy System-on-Chip Design for Portable Diffusion Optical Tomography", Department of Electronics Engineering and Institute of Electronics, National Chiao Tung University (Jun. 2011).

*Primary Examiner* — Mark R Gaworecki
(74) *Attorney, Agent, or Firm* — Edwards Wildman Palmer LLP; Peter F. Corless; Steven M. Jensen

(57) ABSTRACT

A control and sensing system for diffusion optical tomography and a method for operating the same are disclosed. The control and sensing system includes a control unit and a sensing circuit with a plurality of light sources and sensors, each light source being surrounded by a corresponding predetermined number of the sensors. The control unit instructs the light sources to individually emit light to an object, so the object generates a plurality of optical signals, and instructs the predetermined number of the sensors corresponding to each light source to receive the optical signals and transmit them to the control unit, thereby reducing the complexity of the control and sensing system.

10 Claims, 4 Drawing Sheets

CONTROL AND SENSING SYSTEM FOR DIFFUSION OPTICAL TOMOGRAPHY AND METHOD FOR OPERATING THE SAME

CROSS-REFERENCES TO RELATED APPLICATIONS

This application claims under 35 U.S.C. §119(a) the benefit of Taiwanese Application No. 100146129, filed Dec. 14, 2011, the entire contents of which is incorporated herein by reference.

FIELD OF THE INVENTION

The present invention relates to a control and sensing system and a method for operating the same, and more particularly, to a system that emits light to a target and senses it using the optical tomography technique and a method for operating the same.

BACKGROUND OF THE INVENTION

In various current techniques for diagnosing chest or brain tumors, diffusion optical tomography (DOT) has become a popular method for its non-intrusiveness and real-time imaging.

Specifically, diffusion optical tomography utilizes the fact that body tissues or tumors exhibit different optical properties (e.g. absorption, reflection and deflection) to excitation light with specific wavelengths and thus the differences in tissues and inner structure of the human body can be identified. For example, oxygenated and non-oxygenated hemoglobin have different levels of absorption to near-infrared light. Therefore, such characteristics can be used in clinic trials related to blood flow, blood volume and oxygen saturation concentration, and also for determination of body tissues or tumors as just mentioned. Thus, the use of near-infrared light in diffusion optical tomography creates more benefits and extends the application range of the diffusion optical tomography.

In recent years, along with research developments and advances in manufacturing technologies, diffusion optical tomography enables quick operations on the results of image reconstruction, so diagnosis becomes safe and reliable. However, existing diffusion optical tomography is usually realized by large-size machine, which occupies large space and increases power consumption. In particular, circuits for emitting near-infrared light or for detecting optical signals returned by the human tissues or tumors often include a plurality of light sources or sensors so as to emit more light or sense more optical signals. The arrangements for these light sources and sensors are complex, and it is difficult to achieve good detection in limited circuit space.

Moreover, as for the image reconstruction technique used after diffusion optical tomography, in order to meet the requirement for high image resolution, extremely large matrix operations often have to be performed on the tomography results. However, huge matrix operations often results in long imaging time and a bulky system, and real-time scanning and real-time imaging cannot be realized.

SUMMARY OF THE INVENTION

In light of the foregoing drawbacks, the present invention provides a control and sensing system for diffusion optical tomography and a method for operating the same that reduces system complexity while achieving the needs for miniaturization and real-time imaging.

Further, the present invention provides a control and sensing system for diffusion optical tomography, which may include: a control unit for sending out control commands; and a sensing circuit electrically connected to the control unit. The sensing circuit may include: a plurality of light sources for emitting light to an object under test based on the control commands, respectively, so that the object generates a plurality of optical signals in response to the light; and a plurality of sensors for individually receiving the optical signals based on the control commands, and transmitting the optical signals to the control unit, wherein any two adjacent ones of the sensors, any two adjacent ones of the light sources, and each of the sensors with respect to each of the light sources have predetermined distances.

The above sensing circuit may further include a multiplexer and a demultiplexer. The multiplexer is used to enable specific one or more of the light sources based on the control commands of the control unit to emit light to the object. The demultiplexer is to enable specific one or more of the sensors based on the control commands of the control unit to receive the optical signals from the object and transmit them to the control unit.

In addition, the light sources may be arranged in arrays, and each of the plurality of light sources is correspondingly surrounded with a predetermined number of the sensors. The optical signals generated by the object in response to the light may represent biological information of different regions in the object.

The present invention further provides a method for operating a control and sensing system for diffusion optical tomography. The control and sensing system may include a control unit and a sensing circuit including a plurality of light sources and sensors, and each of the plurality of light sources correspond to a predetermined number of the sensors. Compared to the prior art, the method include the steps below: (1) having the control unit send out control commands; and (2) based on the control commands, having the plurality of light sources individually emit light to an object under test, so that the object generates a plurality of optical signals in response to the light, and when the light sources individually emit light to the object, having the control unit instruct the predetermined number of sensors corresponding to each light source to receive the optical signals generated by the object and transmit the received optical signals to the control unit.

The above step (2) may further include: (2-1) determining by the control unit whether the number of the optical signals received has reached the predetermined number, if the number of the optical signals received has not yet reached the predetermined number, then instructing the predetermined number of the sensors corresponding to each of the light sources to continue receiving the optical signals generated by the object in response to the light and transmitting them to the control unit, until the number of optical signals received by the control unit has reached the predetermined number; and (2-2) determining by the control unit whether all the light sources have emitted light to the object, if it is determined that not all of the light sources have emitted light to the object, then instructing those of the light sources having not yet emitted light to emit light to the object, until all of the light sources have emitted light to the object.

Compared to the prior art, the control and sensing system for diffusion optical tomography according to the present invention and the method for operating the same, owing to the sensing circuit have a plurality of carefully-arranged light sources and sensors, achieve the objectives of low cost and miniaturization, and the control unit is able to individually instruct the light sources to emit light to the object and instruct the sensors to receive optical signals, this facilitates the control unit in performing subsequent image processing for diffusion optical tomography.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE EMBODIMENTS

Figure 1:
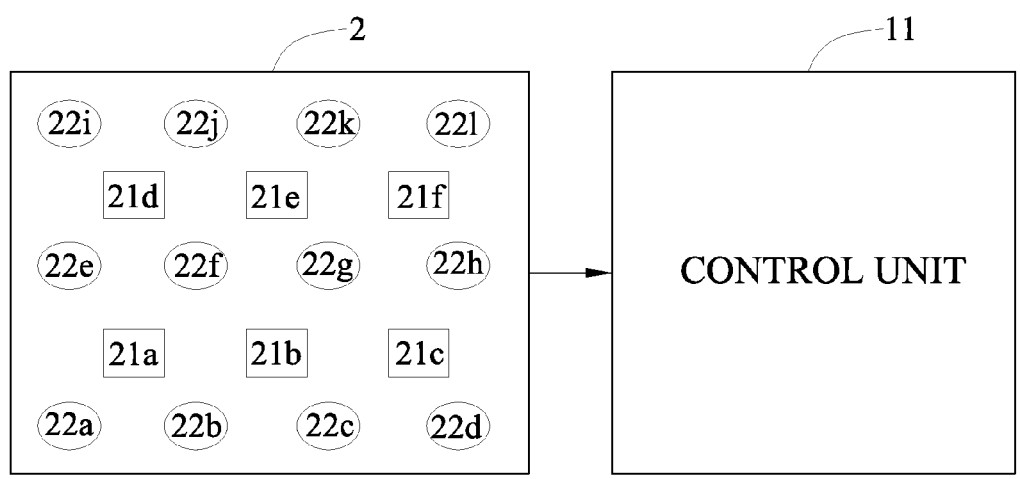
FIG. 1 is a block diagram illustrating a control and sensing system for diffusion optical tomography according to an embodiment of the present invention.

The present invention is described by the following specific embodiments. Those with ordinary skills in the arts can readily understand the other advantages and functions of the present invention after reading the disclosure of this specification. The present invention can also be implemented with different embodiments. Various details described in this specification can be modified based on different viewpoints and applications without departing from the scope of the present invention.

It should be noted that the structures, proportions, sizes and the like shown in the drawings of the present invention are only to accompany the contents disclosed in this specification and to facilitate understanding and reading by those with ordinary skill in the art. They are not to limit the conditions in which the present invention can be embodied, so they have no technical substantial meanings. Any modifications to the structures, proportions, sizes and the like are construed as falling within the scope of the present invention so long as they do not affect the effects generated and the objectives achieved by the present invention. Meanwhile, terms such as "a plurality of" a predetermined number of cited in this specification are to facilitate understanding of the descriptions and are not used to limit the scope of the present invention. Any modifications or changes in relative relationships are construed to be within the scope of the present invention so long as there is no substantial technical change.

Referring to FIG. 1, a block diagram illustrating a control and sensing system for diffusion optical tomography according to an embodiment of the present invention is shown.

As shown in FIG. 1, the control and sensing system includes a control unit 11 and a sensing circuit 2 connected with the control unit 11.

The control unit 11 issues control commands to the sensing circuit 2. The control unit 11 can be provided on a chip in an actual implementation.

The sensing circuit 2 includes a plurality of light sources 21a, 21b, 21c, 21d, 21e and 21f and a plurality of sensors 22a, 22b, 22c, 22d, 22e, 22f, 22g, 22h, 22i, 22j, 22k and 22l.

The light sources 21a, 21b, 21c, 21d, 21e and 21f emit light to an object under test based on the control commands, respectively. The object usually refers to human tissues, such as a tumor. The emitted light can be continuous waves of near-infrared light with a wavelength of 735 nm or 890 nm. It should be noted that the light sources 21a, 21b, 21c, 21d, 21e and 21f do not need to emit light all at the same time, but can emit light separately based on the control commands of the control unit 11. In addition, the light sources 21a, 21b, 21c, 21d, 21e and 21f emits light with the same wavelength in one procedure of the diffusion optical tomography.

The sensors 22a, 22b, 22c, 22d, 22e, 22f, 22g, 22h, 22i, 22j, 22k and 22l each receives optical signals generated by an reaction of the object with the plurality of lights rays emitted by the light sources 21a, 21b, 21c, 21d, 21e and 21f based on the control commands, and transmits them to the control unit 11. These optical signals represent biological information of different regions of the object in response to the light in terms of absorption, reflection, refraction, diffusion or the like.

The sensing circuit 2 can be manufactured onto a flexible printed circuit (FPC) with an area of about 4×6 cm$^2$ in an actual implementation. As shown in FIG. 1, the FPC is provided with six light sources 21a, 21b, 21c, 21d, 21e and 21f and twelve sensors 22a, 22b, 22c, 22d, 22e, 22f, 22g, 22h, 22i, 22j, 22k and 22l, which are arranged in interspersed columns and rows, wherein one light source (e.g. light source 21a) is surrounded by four sensors (e.g. sensors 22a, 22b, 22f and 22e), and the two sensors 22b and 22f are shared between the light sources 21a and 21b. In addition, the sensors 22a, 22b, 22c, 22d, 22e, 22f, 22g, 22h, 22i, 22j, 22k and 22l and the light sources 21a, 21b, 21c, 21d, 21e and 21f are all provided on a side of the FPC facing the object. The intervals among the sensors 22a, 22b, 22c, 22d, 22e, 22f, 22g, 22h, 22i, 22j, 22k and 22l, the intervals among the light sources 21a, 21b, 21c, 21d, 21e and 21f, and the distances between each of the sensors 22a, 22b, 22c, 22d, 22e, 22f, 22g, 22h, 22i, 22j, 22k and 22l and each of the light sources 21a, 21b, 21c, 21d, 21e and 21f have predetermined values. For example, the intervals among the sensors 22a, 22b, 22c, 22d, 22e, 22f, 22g, 22h, 22i, 22j, 22k and 22l may be 2 cm; the intervals among the light sources 21a, 21b, 21c, 21d, 21e and 21f may be 2 cm, and the distances between each of the sensors 22a, 22b, 22c, 22d, 22e, 22f, 22g, 22h, 22i, 22j, 22k and 22l and each of the light sources 21a, 21b, 21c, 21d, 21e and 21f may be 1.414 cm.

Moreover, the sensing circuit 2 may further include a multiplexer and a demultiplexer (not shown), which may be provided at a side of the FPC away from the object. The multiplexer is used to enable specific one(s) of the light sources 21a, 21b, 21c, 21d, 21e and 21f based on the control commands of the control unit 11 so as to emit light to the object. The demultiplexer is used to enable specific one(s) of the sensors 22a, 22b, 22c, 22d, 22e, 22f, 22g, 22h, 22i, 22j, 22k and 22l based on the control commands of the control unit 11 so as to receive the optical signals from the object and transmit them to the control unit 11.

The FPC may be adhered to the body of a user to emit near-infrared light to human tissues or a tumor.

From FIG. 1 and the associated descriptions, it can be understood that the present invention provides a control and sensing system for diffusion optical tomography primarily used on a FPC and designed with a plurality of light sources and sensors arranged in arrays having a predetermined amount, predetermined locations and predetermined intervals. Thus, the complexity of the sensing circuit can be reduced, and more optical signals can be sensed with less light sources in a minimum element area, thereby reducing cost.

Moreover, a method for operating the control and sensing system for diffusion optical tomography includes, firstly, the control unit 11 sends out a control command. Then, based on the control command, the light sources 21*a*, 21*b*, 21*c*, 21*d*, 21*e* and 21*f* emit light to the object, respectively, and when the light sources 21*a*, 21*b*, 21*c*, 21*d*, 21*e* and 21*f* emit light to the object, the control unit 11 instructs a predetermined number of sensors 22*a*, 22*b*, 22*c*, 22*d*, 22*e*, 22*f*, 22*g*, 22*h*, 22*i*, 22*j*, 22*k* or 22*l* corresponding to each of the light sources 21*a*, 21*b*, 21*c*, 21*d*, 21*e* and 21*f* to receive optical signals generated by the object in response to the light, and then transmit the generated optical signal to the control unit 11.

Secondly, in the phase of the light sources 21*a*, 21*b*, 21*c*, 21*d*, 21*e* and 21*f* emitting light and the sensors 22*a*, 22*b*, 22*c*, 22*d*, 22*e*, 22*f*, 22*g*, 22*h*, 22*i*, 22*j*, 22*k* or 22*l* receiving optical signals, the control unit 11 will make a determination on whether the number of optical signals received has reached the predetermined number. If the number of optical signals received by the control unit 11 has not reached the predetermined number, then the control unit 11 instructs the sensors 22*a*, 22*b*, 22*c*, 22*d*, 22*e*, 22*f*, 22*g*, 22*h*, 22*i*, 22*j*, 22*k* or 22*l* corresponding to each of the light sources to continue receiving optical signals generated by the object in response to the light, which are transmitted to the control unit 11, until the number of optical signals received by the control unit 11 has reached the predetermined number. In addition, the control unit 11 further makes a determination on whether all of the light sources 21*a*, 21*b*, 21*c*, 21*d*, 21*e* and 21*f* have emitted light to the object. If not all of the light sources 21*a*, 21*b*, 21*c*, 21*d*, 21*e* and 21*f* have emitted light to the object, then the control unit 11 instructs those of the light sources 21*a*, 21*b*, 21*c*, 21*d*, 21*e* and 21*f* that have not yet emitted light to emit light to the object until all of the light sources 21*a*, 21*b*, 21*c*, 21*d*, 21*e* and 21*f* have emitted light to the object.

Figure 2:
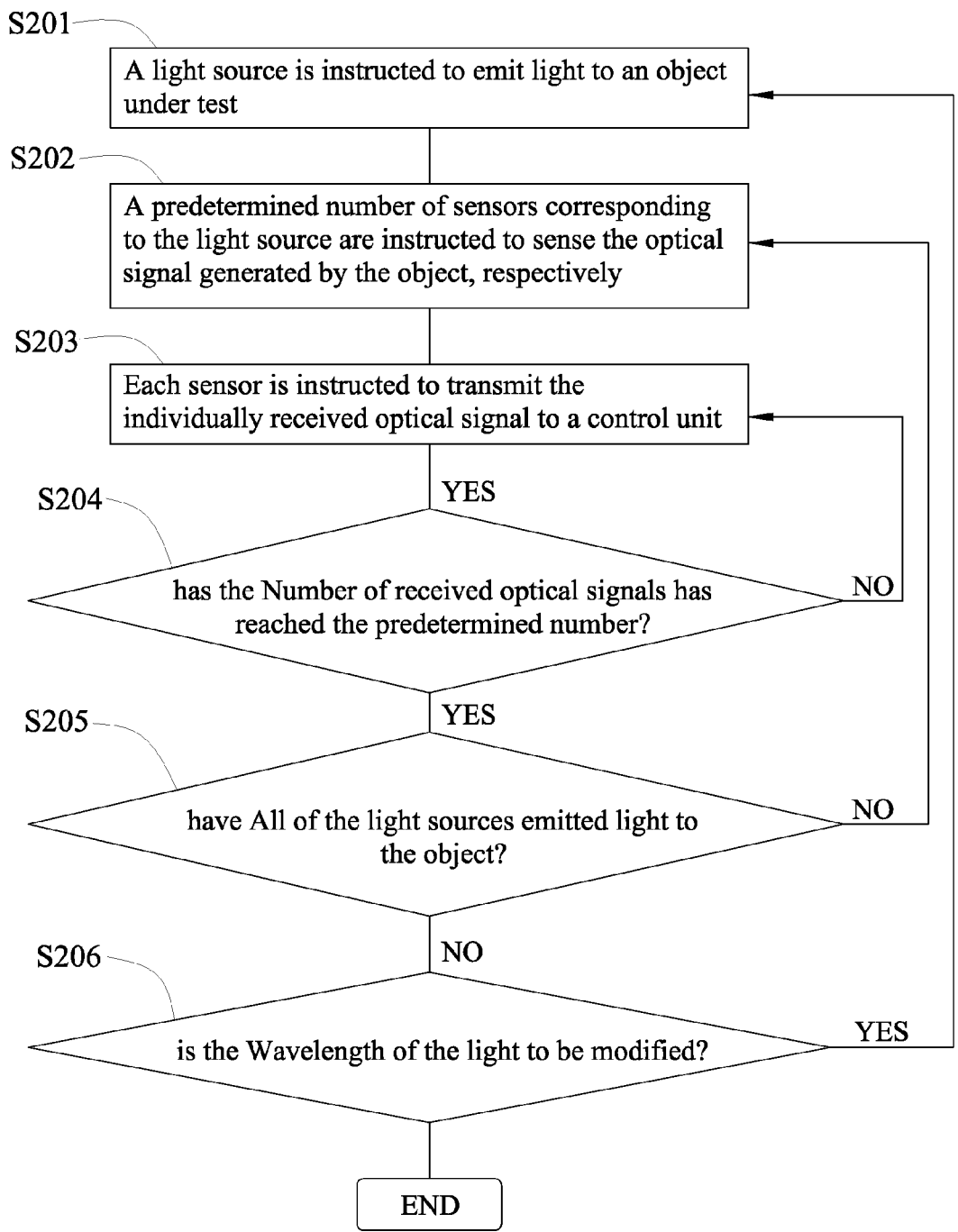
FIG. 2 is a flowchart illustrating an actual implementation of a method for operating the control and sensing system of the present invention.

An actual implementation of the method for operating the control and sensing system of the present invention is shown in FIG. 2. In step S201, a light source is instructed to emit light to an object under test, which generates optical signals in response to the light. In step S202, a predetermined number of sensors corresponding to the light source are instructed to sense the optical signal generated by the object, respectively. In step S203, each sensor is instructed to transmit the individually received optical signal to a control unit. In step S204, the control unit determines whether the number of received optical signals has reached the predetermined number. If so, then proceed to step S205; else, return to step S202. In step S205, the control unit determines if all of the light sources have emitted light to the object. If so, then proceed to step S206; else, return to step S201. In step S206, it is determined if the wavelength of the light is to be modified. If so, then proceed to step S201; else, the process is ended.

As shown in FIG. 1, the control unit 11 can instruct the light sources 21*a*, 21*b*, 21*c*, 21*d*, 21*e* and 21*f* to emit light simultaneously, or instruct just one of them to emit light. Assuming the control unit 11 instructs the light source 21*a* to emit light to the object, the sensors 22*a*, 22*b*, 22*f* and 22*e* are instructed to return sensed optical signals. In this case, there should be four optical signals. If the control unit 11 has not yet received all four optical signals, it will then instruct the one(s) of the sensors 22*a*, 22*b*, 22*f* and 22*e* that have not yet returned optical signals to sense and return optical signals. If the control unit 11 has already received all four optical signals, then another light (e.g. light source 21*b*) is instructed to emit light to the object, and so on.

From the above descriptions of the method for operating the control and sensing system with reference to FIG. 2, it can be understood that the control unit is capable of instructing the individual light source to emit light separately and instruct a predetermined number of sensors corresponding to each light source to sense and return optical signals. Accordingly, light can be emitted to different regions on the object, and optical signals generated by those regions in response to the light can be fully returned for subsequent signal processing for diffusion optical tomography by the control unit.

Figure 3:
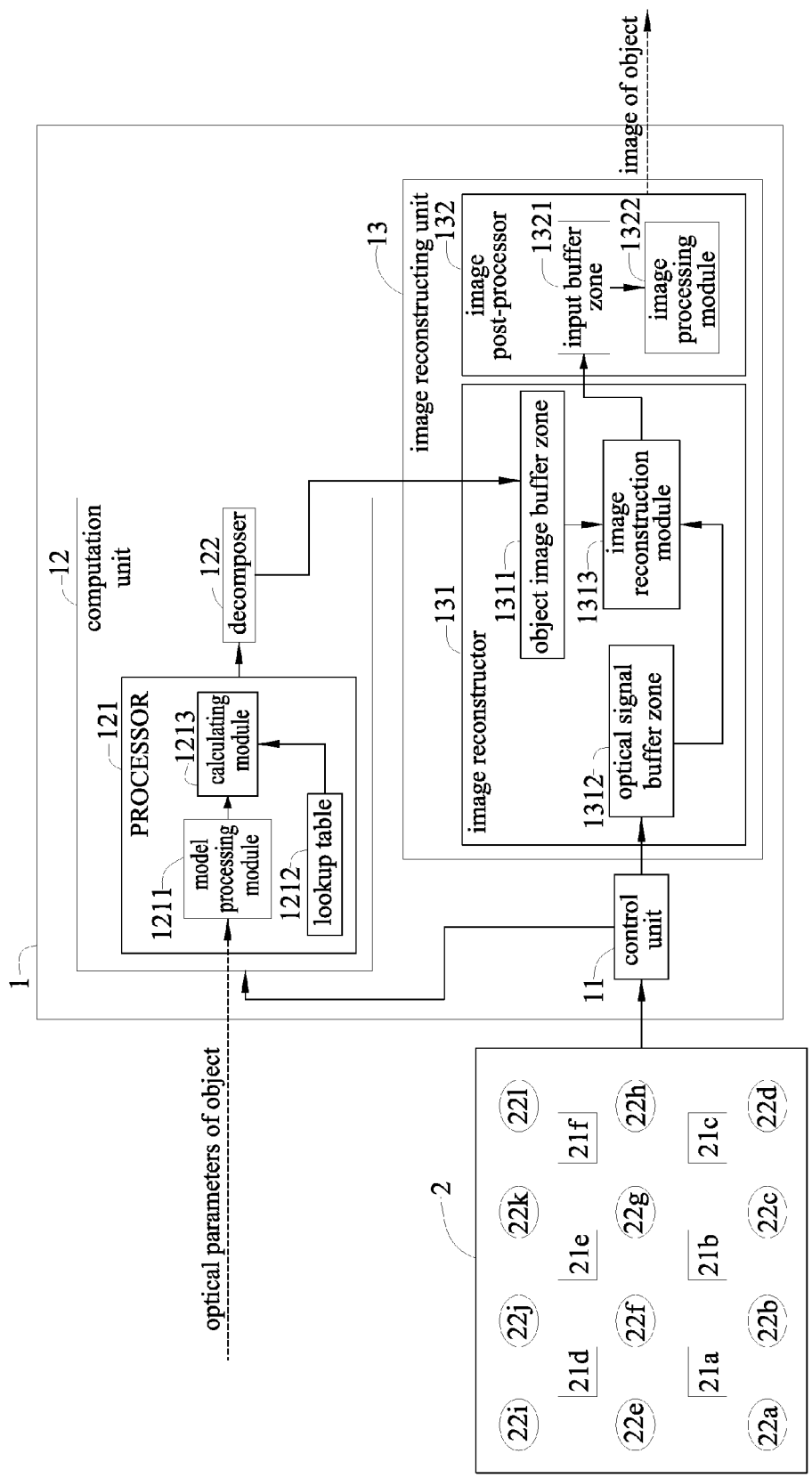
FIG. 3 is a block diagram illustrating an actual implementation of a diffusion optical tomography apparatus according to an embodiment of the present invention.

On the other hand, the control and sensing system for diffusion optical tomography according to the present invention can be a part of a diffusion optical tomography apparatus in an actual implementation. As shown in FIG. 3, a diffusion optical tomography apparatus includes the sensing circuit 2 as mentioned earlier and an optical tomography element 1 electrically connected thereto.

The optical tomography element 1 includes the above control unit 11, a computation unit 12 and an image reconstructing unit 13.

The computation unit 12 includes a processor 121 and a decomposer 122. The processor 121 is used for generating an image model of the object. The image model may describe the situations of light being scattered and diffusiond by the object. The decomposer 122 is used for performing inverse decomposition. The result of decomposition represents the optical characteristics of the object.

The processor 121 may further include a model processing module 1211, a lookup table 1212 and a calculating module 1213. The model processing module 1211 is used to convert optical parameters of the object into factors for matrix calculation. The optical parameters of the object can be inputted via an input interface (not shown) to the model processing module 1211. The lookup table 1212 includes basic information of the sensing circuit, for example, the number of light sources 21*a*, 21*b*, 21*c*, 21*d*, 21*e* and 21*f* and the interval thereof, the number of sensors 22*a*, 22*b*, 22*c*, 22*d*, 22*e*, 22*f*, 22*g*, 22*h*, 22*i*, 22*j*, 22*k* and 22*l* and the interval thereof, the distances between each light source and each sensor, the wavelength of the emitted light and the like. The calculating module 1213 is used for calculating the matrix of the image model of the object based on the factors for matrix calculation and the basic information of the sensing circuit.

The decomposer 122 performs decomposition using singular value decomposition to obtain an inverse solution matrix.

The image reconstructing unit 13 includes an image reconstructor 131 and an image post-processor 132.

The image reconstructor 131 further includes an object image buffer zone 1311, an optical signal buffer zone 1312, and an image reconstruction module 1313. The optical signal buffer zone 1312 is used for buffering the plurality of optical signals. The object image buffer zone 1311 is used for buffering the inverse solution matrix. The image reconstruction module 1313 is used for processing each optical signal through a sub-frame algorithm to obtain sensing data of the object, and obtaining a scalar product of the sensing data and the inverse solution matrix to reconstruct the original image of the object.

The image post-processor 132 further includes an input buffer zone 1321 and an image processing module 1322. The input buffer zone 1321 is used for buffering the original image. The image processing module 1322 performs weighted-array processing on the original image using the Gaussian function to obtain the final image of the object. The final image is then outputted via a display interface (not shown).

Figure 4:
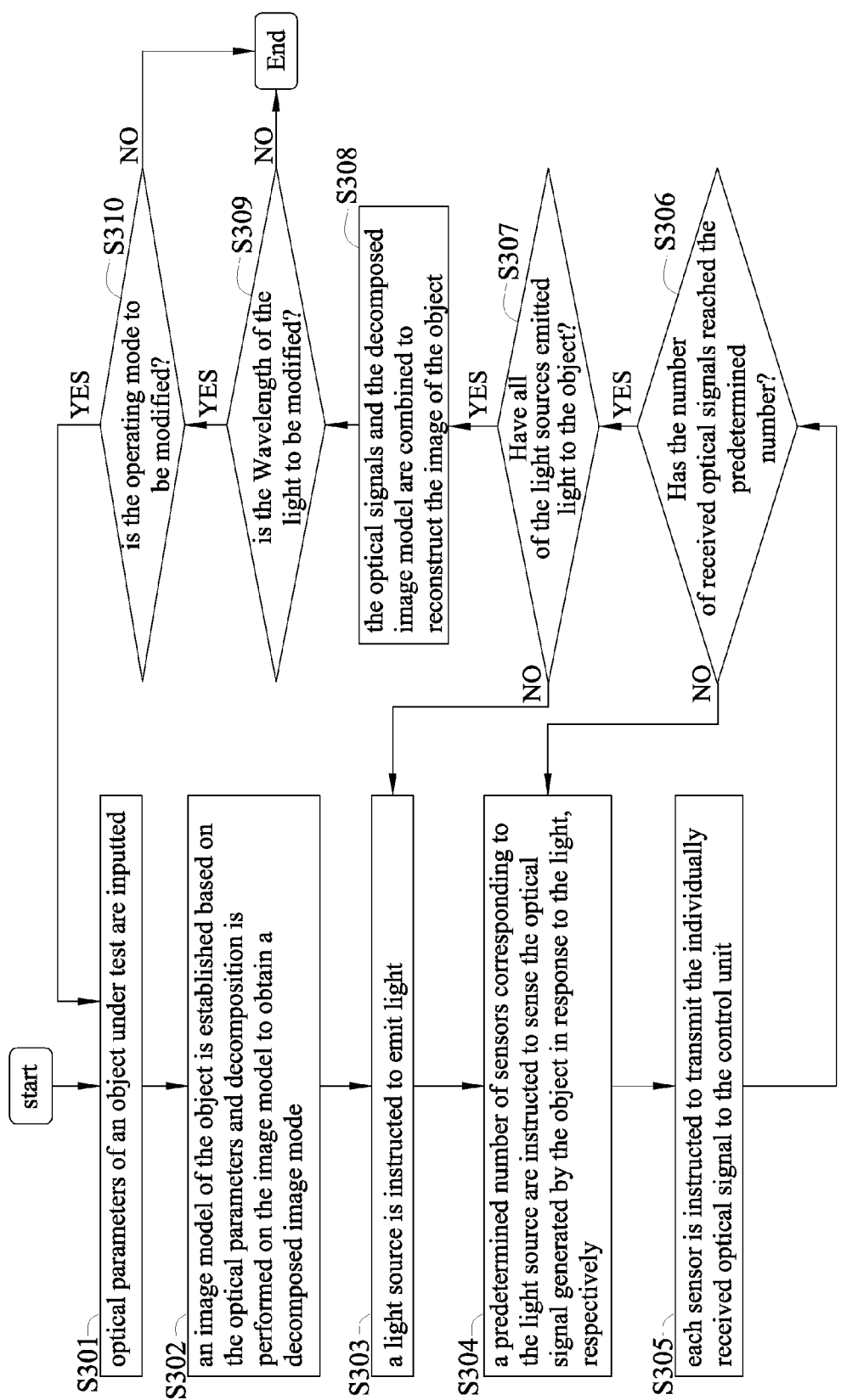
FIG. 4 is a flowchart illustrating an actual implementation of a method for operating the diffusion optical tomography apparatus of the present invention.

An implementation of a method for operating the above diffusion optical tomography apparatus is shown in FIG. 4. It should be noted that the diffusion optical tomography apparatus at least includes a control unit and a sensing circuit having a plurality of light sources and sensors. Each of the light sources corresponds to a predetermined number of sensors.

In step S301, optical parameters of an object under test are inputted. In step S302, an image model of the object is established based on the optical parameters and decomposition is performed on the image model to obtain a decomposed image model. In step S303, a light source is instructed to emit light. In step S304, a predetermined number of sensors corresponding to the light source are instructed to sense the optical signal generated by the object in response to the light, respectively. In step S305, each sensor is instructed to transmit the individually received optical signal to the control unit. Then, proceed to step S306.

In step S306, the control unit determines whether the number of received optical signals has reached the predetermined number. If the number of received optical signals has not yet reached the predetermined number, then return to steps S304 and S305 to allow the predetermined number of sensors corresponding to the light source that have not yet performed sensing, to sense and return optical signals generated by the object in response to the light. If the number of received optical signals has reached the predetermined number, then proceed to step S307.

In step S307, the control unit determines if all of the light sources have emitted light to the object. If the control unit determines that not all of the light sources have emitted light to the object, then return to perform steps S303 to S305, such that any light source that have not yet emitted light is instructed to emit light. If the control unit determines all of the light sources have emitted light to the object, then proceed to step S308. In step S308, the optical signals and the decomposed image model are combined to reconstruct the image of the object. Then, proceed to step S309.

In step S309, the control unit determines if the wavelength of the light is to be modified. If not, the process is ended; alternatively, in order to enhance the image of the object, return back to step S303 again. If the wavelength of the light is to be modified, then modify the wavelength of the light from 735 nm to 890 nm, for example. Then, proceed to step S310.

In step S310, the control unit determines if the operating mode is to be modified. Here this means determining whether optical parameters of an object under test are to be inputted. If so, then return back to step S301 to start again; otherwise, the process is ended, or return to step S303.

In summary, the control and sensing system for diffusion optical tomography according to the present invention mainly includes a control unit and a sensing circuit. The sensing circuit has a plurality of carefully-designed light sources and sensor arrays, so that more optical signals can be received with less light sources, thus achieving the effect of fully sensing an object under test. In addition, the sensing circuit is manufactured onto a FPC, which can be more closely adhered to the body of the user. Furthermore, the plurality of light sources and the sensors are driven by the control unit, such that optical signals generated by the object in response to the light are received to facilitate subsequent image processing for diffusion optical tomography by the control unit.

Therefore, the present invention can be applied to the chest or brain tumor detection, detection of hemorrhagic stroke, verification of cognitive functions in the brain and related medical applications, allowing doctors to quickly grasp the condition of an illnesses or a combination with real-time monitoring in remote care system.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A control and sensing system for diffusion optical tomography, comprising:
    a control unit for sending out control commands; and
    a sensing circuit electrically connected to the control unit, the sensing circuit including:
        a plurality of light sources for emitting light to an object based on the control commands, respectively, so that the object generates a plurality of optical signals in response to the light; and
        a plurality of sensors for individually receiving the optical signals based on the control commands, and transmitting the optical signals to the control unit, wherein intervals among the sensors, intervals among the light sources, and distances between each of the sensors and each of the light sources have predetermined values.

2. The control and sensing system for diffusion optical tomography of claim 1, wherein the sensing circuit further comprises a multiplexer and a demultiplexer, the multiplexer is used to enable specific one or more of the light sources based on the control commands of the control unit to emit light to the object, and the demultiplexer is used to enable specific one or more of the sensors based on the control commands of the control unit to receive the optical signals from the object and transmit them to the control unit.

3. The control and sensing system for diffusion optical tomography of claim 2, wherein the control unit is provided on a chip, and the sensing circuit is formed on a flexible printed circuit (FPC) electrically connected with the chip, and the light sources and the sensors are provided on a side of the FPC facing the object, and the multiplexer and demultiplexer are provided on the other side of the FPC not in contact with the object.

4. The control and sensing system for diffusion optical tomography of claim 1, wherein the light sources are arranged in arrays, and each of the light sources is correspondingly surrounded with a predetermined number of the sensors.

5. The control and sensing system for diffusion optical tomography of claim 1, wherein the optical signals are generated by the object represent biological information of different regions in the object.

6. The control and sensing system for diffusion optical tomography of claim 1, wherein the light emitted by the light sources is continuous waves of near-infrared light.

7. The control and sensing system for diffusion optical tomography of claim 1, wherein the wavelength of the light emitted by the light sources is 735 nm or 890 nm.

8. A method for operating a control and sensing system for diffusion optical tomography, the control and sensing system including a control unit and a sensing circuit including a plurality of light sources and sensors, and each of the light sources corresponding to a predetermined number of the sensors, the method comprising the steps below:
    (1) having the control unit send out control commands; and
    (2) based on the control commands, having the light sources emit light to an object, respectively, so that the object generates a plurality of optical signals in response to the light, and when the plurality of light sources individually emit the light to the object, having the control unit instruct the predetermined number of the sensors corresponding to each light source to receive the optical signals generated by the object and transmit the received optical signals to the control unit.

9. The method for operating a control and sensing system for diffusion optical tomography of claim 8, wherein step (2) further comprises:

(2-1) determining by the control unit whether the number of optical signals received has reached the predetermined number, if the number of optical signals received has not yet reached the predetermined number, instructing the predetermined number of the sensors corresponding to each of the light sources to continue receiving optical signals generated by the object in response to the light and transmitting them to the control unit, until the number of the optical signals received by the control unit has reached the predetermined number; and (2-2) determining by the control unit whether all the light sources have emitted light to the object, if it is determined that not all of the light sources are emitted light to the object, instructing those of the light sources having not yet emitted light to emit light to the object until all of the light sources have emitted light to the object.

10. The method for operating a control and sensing system for diffusion optical tomography of claim 8, further comprising, after step (2), modifying wavelength of the light emitted, and returning to execute steps (1) and (2) again.

* * * * *